US00PP09745P

United States Patent [19]

Harring

[11] Patent Number: Plant 9,745

[45] Date of Patent: Dec. 10, 1996

[54] GERANIUM PLANT NAMED 'HWD GABRIELI'

[75] Inventor: Gabriele Harring, Kerpen, Germany

[73] Assignee: Dummen Jungpflanzenkulturen, Rheinberg-Eversael, Germany

[21] Appl. No.: 520,859

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Gabrieli, characterized by its semi-double salmon flowers; numerous flowers per umbel; and zonation pattern on foliage.

1 Drawing Sheet

The present invention relates to a new and distinct cultivar of geranium plant, botanically known as *Pelargonium×hortorum,* known as the variety Duegabri, and hereinafter referred to by the cultivar name HWD Gabrieli.

The new cultivar is a product of a planned breeding program conducted by the inventor in Rheinberg, Germany. The objective of the breeding program was to develop a new semi-double geranium with salmon flowers and foliage with a zonation pattern.

A new cultivar originated from a cross made by the inventor of the proprietary selection 92-5-2 as the male or pollen parent with the proprietary selection 82-4-1 as the female or seed parent.

The cultivar HWD Gabrieli was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characteristics of HWD Gabrieli. These characteristics in combination distinguish HWD Gabrieli as a new and distinct cultivar.

1. Semi-double salmon flowers.
2. Numerous flowers per umbel.
3. Zonation pattern on foliage.

In Comparison to the parent selection 92-5-2, plants of the new geranium have larger umbels and flower later. In comparison to the parent selection 82-4-1, plants of the new geranium have a more intense zonation pattern on the foliage and smaller umbels.

The new geranium is similar in petal color to the patented cultivar Designer Coral (U.S. Plant Pat. No. 8,522) and the cultivar HWD Corelli (disclosed in the inventor's pending application). In comparison to plants of the cultivar Designer Coral, plants of the new geranium have more salmon (less orange) petal color, shorter peduncles and more flowers per umbel. In comparison to plants of the cultivar HWD Corelli, plants of the new Geranium have more salmon petal color, are less freely branching, fewer umbels per plant, more flowers per umbel, and shorter peduncles.

The accompanying colored photograph illustrates the overall appearance of the new cultivar, showing the colors as true as it is reasonably possible to obtain in colored reproduction of this type. The petal color in the photograph appears lighter than the actual petal color due to light reflectance. The photograph comprises a top perspective view of a typical potted plant of HWD Gabrieli with one plant in a 10-cm container.

The cultivar HWD Gabrieli has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

CLASSIFICATION:

*Botanical.*—*Pelargonium×hortorum.*

*Commercial.*—Zonal geranium.

*Cultivar.*—'HWD Gabrieli'.

Parentage:

*Male parent.*—Proprietary selection 92-5-2.

*Female parent.*—Proprietary selection 82-4-1.

Propagation:

*Type cutting.*—Terminal cuttings.

*Time to initiate roots.*—Summer: 27° C., 21 days; winter: 20° C., 28 days.

PLANT DESCRIPTION:

General appearance: Rounded; upright; freely branching.

Foliage description:

*Arrangement.*—Generally alternate.

*Shape.*—Orbicular with rounded tip and cordate base.

*Size.*—Length: 6.5 cm. Width: 7.5 to 8 cm.

*Texture.*—Velvety; pubescent on upper and under surfaces.

*Margin.*—Crenate.

*Color.*—Young foliage, upper surface: 137A to 137C. Young foliage, under surface: 137C. Mature foliage, upper surface: 137A to 137C. Mature foliage, under surface: 137C. Zonation pattern, upper surface: 137A. Veins, upper surface: 143B. Veins, under surface: 143B. Petiole: 143B.

*Zonation.*—Width of zone: 1.2 to 1.6 cm. Location of zone: 0.5 cm from margin and 1.5 cm from petiole.

*Venation pattern.*—Palmate.

*Petiole.*—Length: 6.5 to 7.5 cm. Diameter: 2.5 mm.

Stem description:

*Internode length.*—0.5 to 1.5 cm.

*Stem color.*—143B.

*Lateral branch number.*—4 to 6.
*Lateral branch length.*—12 to 15 cm.

FLOWERING DESCRIPTION

Flowering habit: Freely flowering. Flowers arranged in umbels.
Natural flowering season: Year-round.
Flowers borne: Flower buds develop in apical leaf axils. Umbels are displayed above the foliage.
Quantity of inflorescences: Very floriferous; usually 8 to 10 open umbels and at least 2 developing umbels per plant at one time.
Umbels:
*Form.*—Rounded.
*Diameter.*—10.5 to 11.5 cm.
*Depth (height).*—8 to 9 cm.
Flowers:
*Form.*—Semi-double.
*Shape.*—Rounded.
*Quantity of flowers per umbel.*—46.
*Diameter.*—4.2 cm.
*Depth (height)*—2 cm.
Petals:
*Shape.*—Obovate with rounded tip.
*Arrangement.*—Rosette, overlapping.
*Quantity.*—5 to 6.
*Aspect.*—Flat.
*Size.*—Length: 2 cm. Width: 1.2 cm.
*Texture.*—Satiny, smooth.
*Margin.*—Entire.
*Color.*—When opening, upper surface: 43C. When opening, under surface: 39D. Upper surface: 43C. Under surface: 39D with streaks of 43C. Fading to: 155D.
Petaloids:
*Shape.*—Irregular, generally obovate with rounded or clifted tip.
*Arrangement.*—Rosette, overlapping.
*Quantity.*—3 to 4.
*Size.*—Length: 1.5 to 2 cm. Width: 1 to 1.5 cm.
*Texture.*—Satiny, smooth.
*Margin.*—Generally entire.
*Color.*—When opening, upper surface: 43C. When opening, under surface: 39D. Upper surface: 43C. Under surface: 39D with streaks of 43C. Fading to: 155D.
Peduncle (umbel stem):
*Angle.*—Erect, some slight bending.
*Length.*—10 cm.
*Pubescence.*—Very fine.
*Color.*—143B.
Pedicel (individual flower stem):
*Angle.*—Erect, rigid.
*Length.*—3 to 4 cm.
*Pubescence.*—Very fine.
*Color.*—143C at base, 63A at apex.
Flower bud:
*Shape.*—Ovoid.
*Length.*—1.1 cm.
*Diameter.*—5 mm.
*Color.*—36D to 155A with development.
Sepals:
*Arrangement.*—Rosette.
*Quantity.*—5.
*Size.*—Length: 9 mm. Width: 2.5 mm.
*Shape.*—Acuminate with apiculate tip.
*Texture.*—Velvety.
*Margin.*—Entire.
*Color.*—Upper surface: 143C. Under surface: 143C.
Reproductive organs:
*Androecium.*—Stamen number: 8. Anther size: 2 mm. Anther color: 184A. Pollen color: 171B.
*Gynoecium.*—Pistil number: 1. Pistil length: 0.8 mm. Stigma shape: Decurrent. Stigma color: 48C. Style length: 4 mm. Style color: 48C.
Ploidy level: Tetraploid.
Disease resistance: No fungal, bacterial nor viral problems observed.
Seed development: Seed production is very rarely observed.

It is claimed:

1. A new and distinct cultivar of geranium plant named HWD Gabrieli, as illustrated and described.

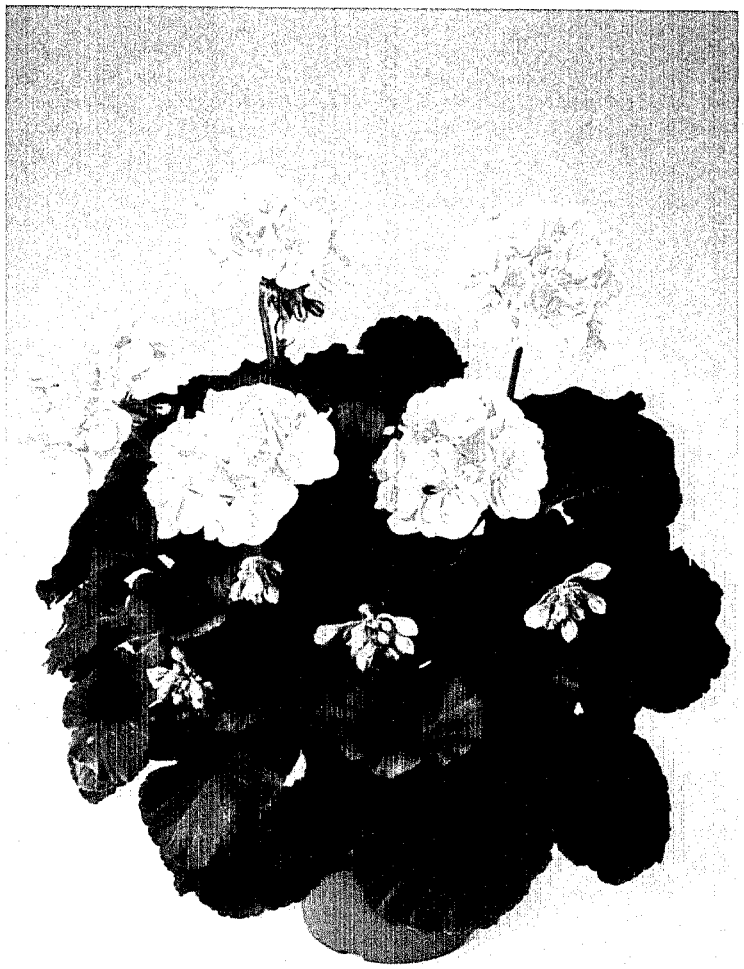

* * * * *